(12) United States Patent
Sheppard

(10) Patent No.: US 8,211,677 B2
(45) Date of Patent: Jul. 3, 2012

(54) VISIBLE LIGHT-ENHANCED ENZYMATIC PROMOTION OF HYDROCARBON REACTIONS

(75) Inventor: Norman John Sheppard, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 12/907,119

(22) Filed: Oct. 19, 2010

(65) Prior Publication Data

US 2011/0097774 A1    Apr. 28, 2011

Related U.S. Application Data

(60) Provisional application No. 61/254,810, filed on Oct. 26, 2009.

(51) Int. Cl.
*C12P 7/04* (2006.01)
*C12P 7/16* (2006.01)
*C12P 7/06* (2006.01)

(52) U.S. Cl. .................. 435/157; 435/160; 435/161

(58) Field of Classification Search .................. None
See application file for complete search history.

(56) References Cited

U.S. PATENT DOCUMENTS

2004/0063568 A1\* 4/2004 Kuhnle et al. .................. 502/60
2005/0059128 A1\* 3/2005 Arnold et al. ................. 435/189
2008/0293101 A1\* 11/2008 Peters et al. ................. 435/69.1

OTHER PUBLICATIONS

Petersen, M. Phytochem. vol. 45, No. 6. pp. 1165-1172, 1997.\*
Araki et al. Rev. Schi. Instrum. 68 (3), pp. 1365-1368, Mar. 1997.\*
Groves, JT. J. Porphyrins Phthalocyanines 4, 350-352, 2000.\*

\* cited by examiner

*Primary Examiner* — Chris R Tate
*Assistant Examiner* — Douglas F White
(74) *Attorney, Agent, or Firm* — Abelman, Frayne & Schwab

(57) ABSTRACT

A photocatalytic method for the hydroxylation of alkanes involving the use of a Cytochrome P450 class of enzyme as a catalyst which is activated by exposure to a pulsed blue light emitted from a light emitting diode (LED) at 450 nm±25 nm.

3 Claims, No Drawings

VISIBLE LIGHT-ENHANCED ENZYMATIC PROMOTION OF HYDROCARBON REACTIONS

CROSS REFERENCE TO RELATED APPLICATIONS

This application claims the benefit of U.S. Application Ser. No. 61/254,810, filed Oct. 26, 2009.

BACKGROUND OF THE INVENTION

This invention relates to the enzymatic hydroxylation of organic compounds and, more particularly, to the light activation of certain naturally-occurring or synthetic enzymes to serve as catalysts in redox reactions involving hydrocarbons.

FIELD OF THE INVENTION

The petroleum industry has long sought a cost-effective process of converting gaseous and relatively unreactive carbon species, for example, aliphatic alkanes, such as methane, ethane, butane and propane, into more reactive, easier-to-transport species that are liquid at room temperature and pressure, i.e. methanol, ethanol, butanol and propanol. Current state-of-the-art technology achieves the foregoing by using zeolite catalysts at elevated temperature and pressure with a feed stock of aliphatic alkanes. A commercial example is the Gas-to-Liquids (GTL) Fischer-Tropsch conversion developed by a South African company, SASOL, and which has been further developed by the Shell Oil Company, among others.

It has been known for some years that there exist a class of enzymes, which are known collectively as Cytochrome P450 (CYP450), which occur throughout nature and are known to promote metabolic pathways in a wide range of mammalian fauna, as well as in fungi, yeast and bacteria. It is also known that Cytochrome P450 can promote valuable and useful chemical transformations in normal paraffins, which are also referred to as aliphatic alkanes. The catalytic photochemical functionalization of alkanes by polyoxometalates is known from U.S. Pat. No. 4,839,008, for example, which is incorporated herein by reference. However, there have always been practical problems associated with supplying the appropriate chemical moieties to achieve a redox reaction.

The hydroxylation reaction promoted by a CYP450 enzyme is essentially a redox reaction, which is similar in its overall pathway to chemical photosynthesis by plant life on earth.

For example, Shelnutt, U.S. Pat. No. 4,917,784, which is incorporated herein by reference, discloses the use of light in the presence of molecular oxygen to achieve the oxidation portion of the CYP450 redox cycle. However, the '784 patent also notes that for the reduction part of the cycle, strong reducing agents such as Zn, NaBH4, and $H_2$ have been employed to break the O—O bond and provide the reactive Fe—O intermediate moiety. A simple example of such a hydroxylation reaction is the conversion of methane to methanol. This is an important reaction since methanol is a starting point for many important synthesis reactions in the petrochemical industry. Also, methanol and its homologues, namely, ethanol, propanol and butanol, are increasingly in demand as "carbon-light" transportation fuels.

More recently, synthetic versions of CYP450 enzyme have been developed (bio-mimetics), which mimic both the structure and the catalytic abilities of naturally occurring Cytochrome P450. One of the remaining problems, however, is that the speed of reaction of such energy-efficient enzymes is still very slow when compared with conventional industrial processes which typically operate at 600° C. and 300 atmospheres pressure.

In an effort to enhance the reaction speed and specificity of the CYP450 enzyme, WO/2007/052049, assigned to Astra Zeneca, and which is incorporated herein by reference, discloses the bio-engineering of the ligands of CYP450.

SUMMARY OF THE INVENTION

It is an object of the present invention to provide effective enhancement of the CYP450 class of enzymes at normal temperature and pressure to enable them to effectively catalyze hydroxylation reactions involving hydrocarbons at ambient temperatures and pressures.

It is another object of the present invention is to employ synthetic versions of CYP450 as a catalyst in hydroxalation reactions in which alkanes are converted to alcohols at normal temperature and pressure.

It is still another object of the present invention to effectively and efficiently promote the reaction of a relatively unreactive aliphatic alkane in a gaseous state to a more reactive, easier to transport liquid species using CYP450 as a catalyst.

The subject invention provides for a photochemical hydroxylation method for producing alcohols from alkanes by the excitation of a natural or synthetic Cytochrome P450 enzyme with a light emitting diode (LED).

DETAILED DESCRIPTION OF THE INVENTION

It has been unexpectedly found that the Cytochrome P450 enzyme can function as an effective catalyst at room temperature and ambient pressure in the reduction part of the CYP450 hydroxylation reaction of alkanes, such as methane, ethane, propane and butane to their corresponding alcohols, namely methanol, ethanol, propanol and butanol by exposing the Cytochrome P450 to appropriately timed bursts of intense blue light at 450 nm±25 nm wavelength, using an energy-efficient light emitting diode (LED). The blue light emitted at the specified wavelength of 450 nm±25 nm is capable of being produced by commercially available LEDs made from an IndiumGalliumNitride (InGaN) composition. Such LED's are disclosed in Review of Scientific Instruments, 68, 1365 (1997), and is incorporated herein by reference.

The catalytic activity of the Cytochrome P450 class of enzymes is substantially increased in the presence of light in the prescribed wavelength range, thereby driving the hydroxylation reaction in favor of more rapid completion.

P450 Cytochromes which may be classified as a diverse range of mono-oxygenase enzymes, all exhibit a so-called Soret peak at about 450 nm wavelength in their reduced form when saturated with carbon monoxide. The Soret peak is an intense peak in the blue wavelength of the visible spectrum and corresponds to the wavelength of very strong absorption by the vividly-pigmented metal-containing moieties, such as the various cytochromes discussed herein.

In an embodiment of the invention wherein blue light emitted by an LED is used to drive the reduction part of the CYP450 hydroxylation, a significant benefit is that LED's may be switched on and off, thus allowing the duration of exposures to be accurately controlled. This permits more precise control of the reaction steps while avoiding the need of using strong, reactive, difficult-to-handle chemical reducing agents.

Another benefit to be realized by another embodiment of the method of the invention is the ability to incorporate the blue LED's into the polymer membrane that encapsulates the CYP450 enzyme and its associated zeolite, the so-called "zeozyme". In this manner, good photon flux is promoted from the LED's to the reaction sites.

The replacement of the natural catalytic reaction site in cytochrome P-450 (made of iron porphyrin) with the more stable iron phthalocyanine, as well as replacing the protein sheath around the reactive site with the porous mineral zeolite, are disclosed in Jacobs, Nature, No. 370, 1994, 541-544, which is incorporated herein by reference. The chemical mimicry of cytochrome P-450 by zeolite encapsulated metalloporphyrins ("zeozymes") is disclosed in Bizeng et al. Journal of Inorganic Biochemistry, Vol. 67, No. 1, July 1997, pg. 101, which is incorporated herein by reference.

In another embodiment of the invention, improved specificity at the reaction site is realized by fine-tuning of the exact wavelength in the range of 425-475 nanometers, to correspond with the excitation energy of the relevant ligands. This promotes reactions at the specifically desired sites, especially at the terminal C—H bond, to complete the hydroxylation of the target alkane molecule. By using a specific wavelength of light that corresponds, i.e., resonates, with the vibration frequency of the ligand to be activated, i.e., reduced, the specificity of the hydroxylation reaction at the desired site is enhanced.

Yet another benefit to be realized by an embodiment of the present invention is the nanosecond control which is attainable with LED's, which makes the invention useful on an industrial scale by virtue of being able to fine-tune the LED/ (light-dark) cycle to the reactor flow rate and reaction kinetics. This drives forward, i.e., increases the rate constants, the desired hydroxylation reaction of C—H to C—OH.

While the invention has been described in sufficient detail for those skilled in the art to make and use it, these details are not intended to limit the scope of the invention as defined in the appended claims.

What is claimed is:

1. A photochemical method of converting aliphatic alkanes to alcohols, which comprises:
    subjecting an aliphatic alkane to a redox reaction by contacting the alkane with a CYP450 enzymatic catalyst, which is in a zeolite material encapsulated in a polymeric membrane, with an intermittently pulsed blue light from a light-emitting diode (LED) at a wavelength of 450 nm±25 nm to excite the CYP450 catalyst and drive the redox reaction to completion; and
    recovering an aliphatic alcohol.

2. The method of claim 1 wherein the alkane is selected from the group consisting of methane, ethane, propane and butane.

3. The method of claim 1, wherein the alcohols are selected from the group consisting of methanol, ethanol, propanol and butanol.

\* \* \* \* \*